United States Patent
Ko et al.

(10) Patent No.: US 6,939,410 B2
(45) Date of Patent: Sep. 6, 2005

(54) APPARATUS AND METHOD FOR COLLECTING IMPURITIES ON A SEMICONDUCTOR WAFER

(75) Inventors: Yong-Kyun Ko, Osan (KR); Byung-Woo Son, Yongin (KR); Jong-Cheol Jeong, Gyeonggi-do (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 9 days.

(21) Appl. No.: 10/779,642

(22) Filed: Feb. 18, 2004

(65) Prior Publication Data

US 2004/0163670 A1 Aug. 26, 2004

(30) Foreign Application Priority Data

Feb. 21, 2003  (KR) ................................ 10-2003-0011109

(51) Int. Cl.⁷ ................................................ B08B 3/04
(52) U.S. Cl. ............................... 134/3; 134/26; 134/28; 134/32; 134/33; 134/36; 134/95.1; 134/95.2; 134/148; 134/153; 134/181; 134/902
(58) Field of Search ................................ 134/3, 26, 28, 134/32, 33, 36, 148, 153, 181, 902, 95.1, 95.2

(56) References Cited

U.S. PATENT DOCUMENTS

| | | | |
|---|---|---|---|
| 5,569,328 A | * 10/1996 | Petvai et al. | ................. 118/696 |
| 6,053,984 A | * 4/2000 | Petvai et al. | ................. 134/3 |
| 6,182,675 B1 | 2/2001 | Naka et al. | |
| 6,517,641 B2 | * 2/2003 | Fernandez | ................. 134/33 |
| 2002/0134406 A1 | 9/2002 | Heo et al. | |

FOREIGN PATENT DOCUMENTS

| JP | 10-242228 | 9/1998 |
|---|---|---|
| KR | 2002-0074757 | 10/2002 |

* cited by examiner

Primary Examiner—Zeinab El-Arini
(74) Attorney, Agent, or Firm—Lee & Morse, P.C.

(57) ABSTRACT

An apparatus for collecting impurities on a semiconductor wafer includes an airtight process chamber, a rotary chuck disposed in the process chamber for rotating and horizontally supporting the semiconductor wafer, a first scanning unit for forming a droplet of a first scanning solution and for scanning an upper surface of the semiconductor wafer rotated by the rotary chuck with the droplet to collect first impurities, a driving unit for tilting the rotary chuck and the semiconductor wafer supported on the rotary chuck, and a second scanning unit for receiving a second scanning solution for collecting second impurities from an edge portion of the semiconductor wafer, the second scanning solution being in contact with the edge portion of the semiconductor wafer tilted by the driving unit and rotated by the rotary chuck so that the second scanning solution scans the edge portion of the semiconductor wafer.

20 Claims, 14 Drawing Sheets

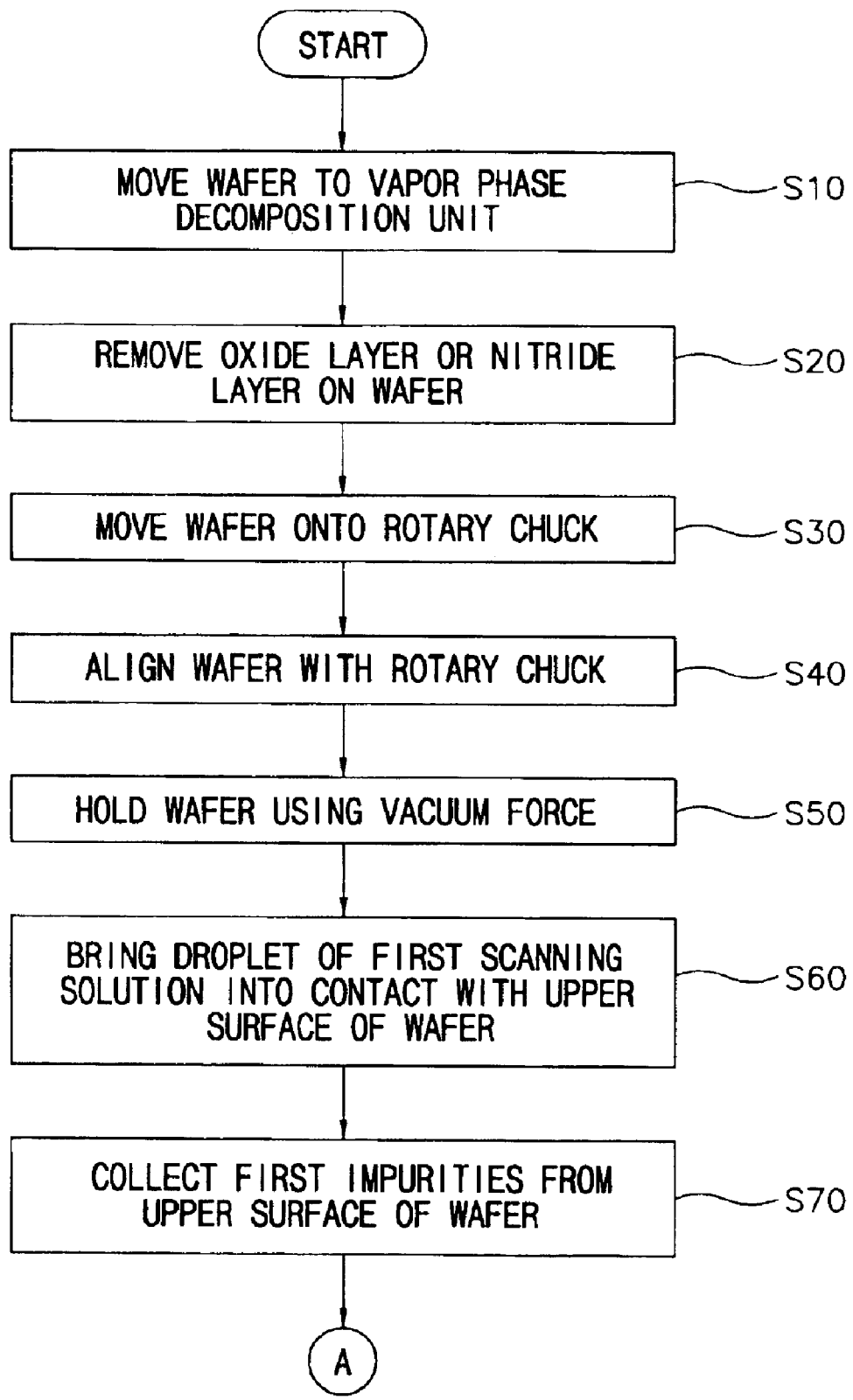

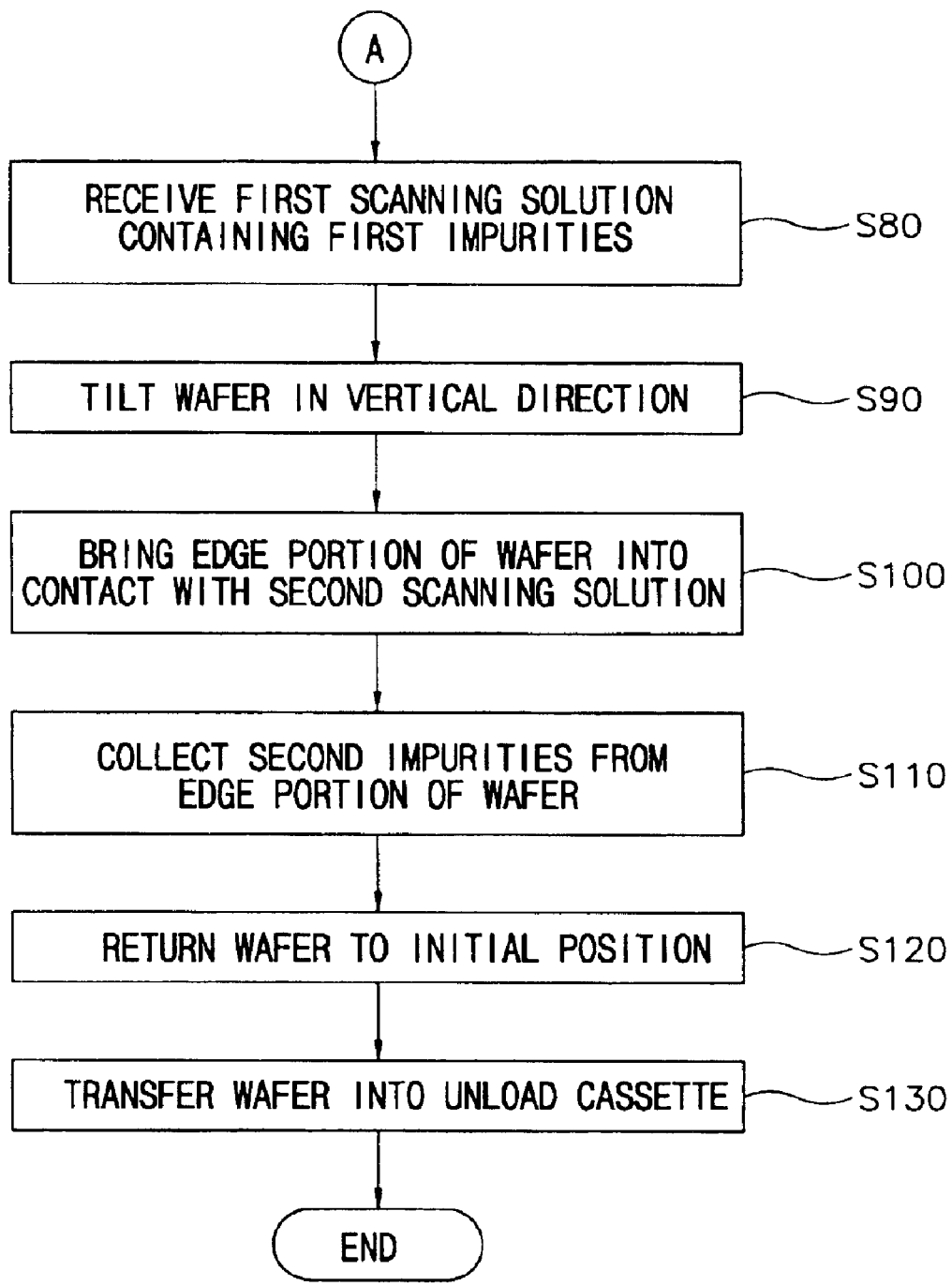

APPARATUS AND METHOD FOR COLLECTING IMPURITIES ON A SEMICONDUCTOR WAFER

BACKGROUND OF THE INVENTION

1. Field of the Invention

The present invention relates to an apparatus and a method for collecting impurities on a semiconductor wafer. More particularly, the present invention relates to an apparatus and a method for collecting metallic impurities remaining on a semiconductor wafer using a scanning solution.

2. Description of the Related Art

Generally, semiconductor devices are manufactured through a three-step process. First, a fabrication process is performed for forming electronic circuits on a semiconductor wafer. Second, an electrical die sorting (EDS) process is performed for inspecting electrical characteristics of the semiconductor devices on the semiconductor wafer. Third, a packaging process is performed for packaging the semiconductor devices in epoxy resins and individuating the semiconductor devices.

The fabrication process may include a deposition process for depositing a layer on the semiconductor wafer, a chemical mechanical polishing (CMP) process for planarizing a surface of the layer, a photolithography process for forming a photoresist pattern on the layer, an etching process for forming an electrical pattern using the photoresist pattern, an ion implantation process for implanting predetermined ions into predetermined portions of the semiconductor wafer, a cleaning process for removing impurities from the semiconductor wafer, an inspection process for inspecting the surface of the semiconductor wafer on which the layer or the pattern is formed, or other similar processes.

Impurities, such as metallic contaminants, remain on the semiconductor wafer during the fabrication process. The impurities cause deterioration in the performance of the semiconductor devices, as well as lower yields in the manufacturing of the semiconductor devices. Recently, as the degree of integration of the semiconductor devices has increased, an analysis process on the impurities has become increasingly important in the manufacturing of the semiconductor devices.

The analysis process on the impurities remaining on the semiconductor wafer includes a process for collecting the impurities and a process for analyzing a sample containing the impurities.

For example, in a conventional apparatus and method for collecting metallic impurities on a semiconductor wafer, the apparatus includes a process chamber including a loading unit for loading the semiconductor wafer and an unloading unit for unloading the semiconductor wafer, a vapor phase decomposition disposed in the process chamber for decomposing a silicon oxide layer on the semiconductor wafer, and a scanning unit disposed in the process chamber for scanning the semiconductor wafer to collect metallic impurities.

An impurity sample acquired by the impurity collection apparatus contains various types of metallic impurities, and may then be analyzed using an analysis apparatus, such as an atomic absorption spectroscope, an inductively coupled plasma (ICP) mass spectroscope, a total X-ray fluorescent analyzer, or the like.

However, the conventional impurity collection apparatus is not able to collect impurities from an edge portion of the semiconductor wafer. Accordingly, there is a need for an improved apparatus and method for collecting impurities on the semiconductor wafer.

SUMMARY OF THE INVENTION

According to embodiments of the present invention, an apparatus and method are provided, in which impurities are collected from both a front surface and an edge portion of a semiconductor wafer.

It is therefore a feature of an embodiment of the present invention to provide an apparatus for collecting impurities on a semiconductor wafer including an airtight process chamber, a rotary chuck disposed in the process chamber for horizontally supporting the semiconductor wafer thereon and for rotating the semiconductor wafer, a first scanning unit for forming a droplet of a first scanning solution and for scanning an upper surface of the semiconductor wafer rotated by the rotary chuck with the droplet of the first scanning solution to collect first impurities from the upper surface of the semiconductor wafer, a driving unit for tilting the rotary chuck to tilt the semiconductor wafer supported on the rotary chuck, and a second scanning unit for receiving a second scanning solution in order to collect second impurities from an edge portion of the semiconductor wafer, the second scanning solution received in the second scanning unit being in contact with the edge portion of the semiconductor wafer tilted by the driving unit and rotated by the rotary chuck so that the second scanning solution scans the edge portion of the semiconductor wafer.

The apparatus may further include a second driving unit for moving the rotary chuck in horizontal and vertical directions. The first scanning unit preferably includes a scanning nozzle for forming the droplet of the first scanning solution and a scanning robot coupled to the scanning nozzle for horizontally moving the scanning nozzle so that the droplet of the first scanning solution scans the upper surface of the semiconductor wafer. The scanning robot may be a SCARA type robot.

A circular hole for receiving the first scanning solution may be formed through the scanning nozzle, and a coupling groove for coupling the scanning nozzle to a scanning arm of the scanning robot may also be formed at an inner surface of the circular hole adjacent to an upper surface of the scanning nozzle. A concave portion is preferably formed at a lower surface of the scanning nozzle for making contact with the droplet of the first scanning solution.

Preferably, the scanning arm has a coupling section coupled to the coupling groove, an air channel being in communication with the circular hole and for providing an air pressure in order to form the droplet of the first scanning solution that coheres to a lower surface of the nozzle, and a nozzle-removing section for removing the scanning nozzle from the coupling section. The nozzle-removing section preferably includes a second air channel for providing a second air pressure in order to remove the scanning nozzle from the coupling section, a rod disposed in the second air channel for removing the scanning nozzle, a piston connected to the rod for transmitting the second air pressure to the rod so that the rod protrudes outwardly from the second air channel and then pushes the scanning nozzle coupled with the coupling section and a return spring for returning the rod protruded by the second air pressure. The apparatus may further include a nozzle tray for supporting a plurality of the scanning nozzles and a storage container for storing the first scanning solution.

The apparatus may further include a plurality of sampling cups for receiving the first scanning solution containing the first impurities and a sampling cup tray for supporting the plurality of sampling cups.

The second scanning unit preferably includes a plurality of scanning containers for receiving the second scanning solution, a scanning container tray for supporting the plurality of scanning containers, the scanning container tray having a disc shape, and the plurality of scanning containers being circumferentially disposed along an edge portion of the scanning container tray and a second driving unit for rotating the scanning container tray. Each of the plurality of scanning containers preferably has a scanning groove, and a bottom surface of the scanning groove is preferably a curved surface corresponding to the edge portion of the semiconductor wafer.

Alternatively, the second scanning unit may include a plurality of scanning containers for receiving the second scanning solution, a scanning container tray for supporting the plurality of scanning containers, a scanning container stage disposed under the semiconductor wafer tilted by the driving unit for supporting one of the scanning containers and a transfer robot for transferring the scanning containers between the scanning container tray and the scanning container stage.

The apparatus may further include a load cassette disposed in the process chamber for receiving a plurality of semiconductor wafers to be subjected to an impurity collection process and an unload cassette disposed in the process chamber for receiving the plurality of semiconductor wafers subjected to the impurity collection process.

There may be a vapor phase decomposition unit for removing an oxide layer or a nitride layer formed on the semiconductor wafer using a hydrofluoric acid vapor. The vapor phase decomposition unit preferably includes an airtight container capable of opening and closing in which the hydrofluoric acid vapor is supplied and a load plate disposed in the airtight container for supporting the semiconductor wafer. The apparatus may further include a transfer robot for transferring the semiconductor wafer among the load cassette, the vapor phase decomposition unit, the rotary chuck and the unload cassette.

The apparatus may further include an aligner for aligning a center of the semiconductor wafer supported on the rotary chuck with a central axis of the rotary chuck, the aligner preferably including a plurality of alignment pins for simultaneously moving horizontally toward the central axis of the rotary chuck so that the center of the semiconductor wafer is aligned with the central axis of the rotary chuck and a second driving unit disposed over the rotary chuck for moving the plurality of alignment pins in horizontal and vertical directions.

The first and second scanning solutions preferably include $H_2O$, $H_2O_2$ and HF.

It is a feature of another embodiment of the present invention to provide a method for collecting impurities on a semiconductor wafer including rotating the semiconductor wafer, scanning an upper surface of the semiconductor wafer with a droplet of a first scanning solution in order to collect first impurities from the upper surface of the semiconductor wafer, receiving the first scanning solution containing the first impurities into a sampling cup, tilting the semiconductor wafer so that an edge portion of the semiconductor wafer is in contact with a second scanning solution received in a scanning container, and rotating the tilted semiconductor wafer in order to collect second impurities from the edge portion of the semiconductor wafer.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIGS. 14A and 14B, collectively, is a flow chart for illustrating a method for collecting impurities on a semiconductor wafer using the apparatus for collecting impurities as shown in FIG. 1.

DETAILED DESCRIPTION OF THE INVENTION

Korean Patent Application No. 2003-11109, filed on Feb. 21, 2003, and entitled: "Apparatus and Method For Collecting Impurities on a Semiconductor Wafer," is incorporated by reference herein in its entirety.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
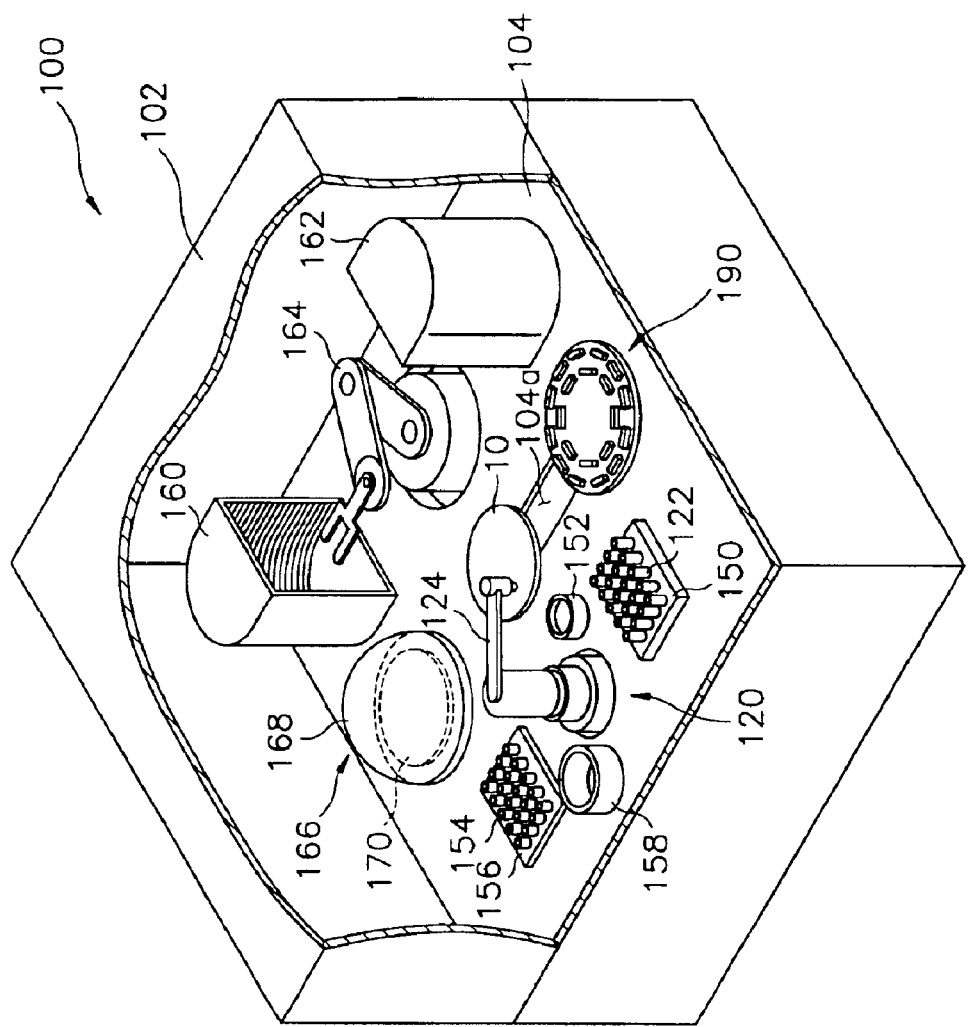
FIG. 1 illustrates a perspective view of an apparatus for collecting impurities according to an embodiment of the present invention.
Figure 2:
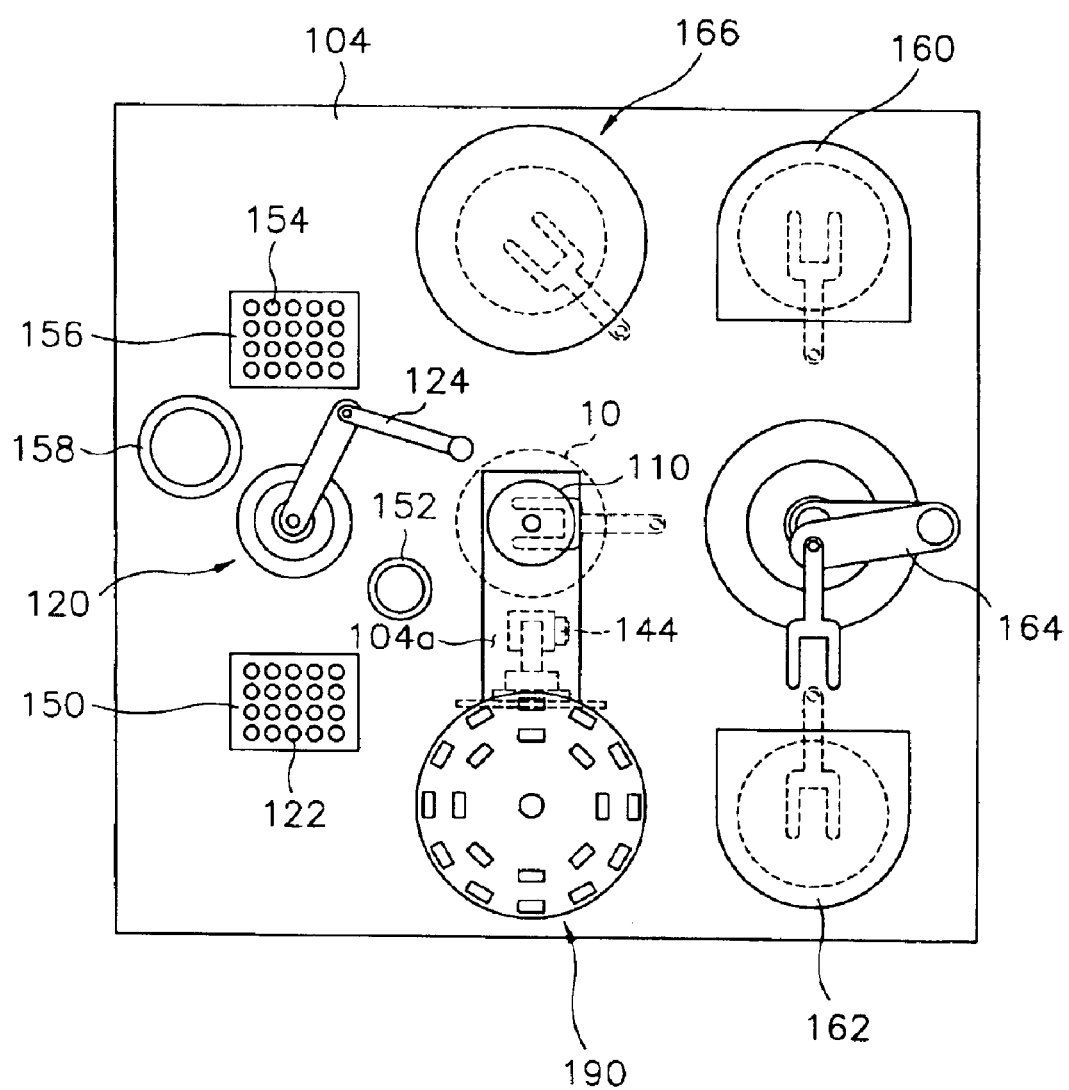
FIG. 2 illustrates a plan view of the apparatus for collecting impurities shown in FIG. 1.

FIG. 1 illustrates a perspective view of an apparatus for collecting impurities according to one embodiment of the present invention. FIG. 2 illustrates a plan view of the apparatus for collecting impurities shown in FIG. 1.

Referring to FIGS. 1 and 2, an apparatus 100 for collecting impurities preferably includes an airtight process chamber 102, a rotary chuck 110, a first scanning unit 120, a first driving unit 144, and a second scanning unit 190.

A base panel 104 for supporting these elements is horizontally disposed in a central portion of the process chamber 102. The rotary chuck 110 is disposed over a penetrating hole 104a of the base panel 104 in the process chamber 102, and supports a semiconductor wafer 10 in a horizontal direction. In addition, the rotary chuck 110 holds the semiconductor wafer 10 using a vacuum force, and rotates the semiconductor wafer 10.

The first scanning unit 120 sucks a first scanning solution, and then forms a droplet of the first scanning solution. In addition, the first scanning unit 120 moves horizontally so that the droplet of the first scanning solution scans an upper surface of the semiconductor wafer 10. The droplet of the first scanning solution is in contact with the upper surface of the semiconductor wafer 10 being rotated by the rotary chuck 110 to collect first impurities from the upper surface of the semiconductor wafer 10.

The first driving unit 144 tilts the rotary chuck 110 so that the semiconductor wafer 10 supported on the rotary chuck 110 is disposed in a vertical direction.

The second scanning unit 190 receives a second scanning solution for collecting second impurities from an edge portion of the semiconductor wafer 10. A lower edge portion of the tilted semiconductor wafer 10 is in contact with the second scanning solution received in the second scanning unit 190. The rotary chuck 110 rotates the tilted semiconductor wafer 10 so that the second scanning solution received in the second scanning unit 190 scans the edge portion of the semiconductor wafer 10.

The first scanning solution and the second scanning solution may include $H_2O$, $H_2O_2$, and HF. Preferably, the first scanning solution and the second scanning solution may include $H_2O$, $H_2O_2$, and HF in a ratio of about 95:4:1, respectively.

The first impurities and the second impurities may include metallic impurities such as lithium (Li), boron (B), sodium (Na), iron (Fe), copper (Cu), calcium (Ca), chromium (Cr), aluminum (Al), nickel (Ni), zinc (Zn), tungsten (W), lead (Pb), barium (Ba), magnesium (Mg), arsenic (As), or the like.

Figure 3:
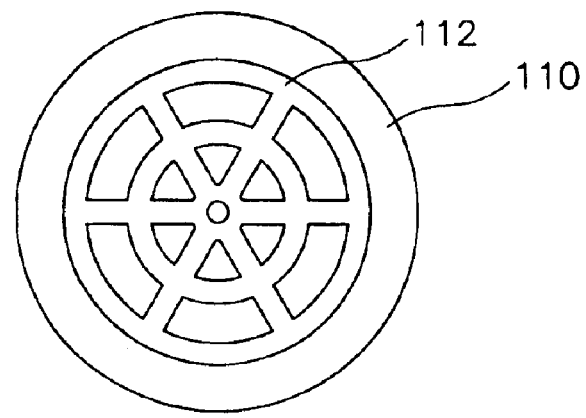
FIG. 3 illustrates a plan view of a rotary chuck as shown in FIG. 1.
Figure 4:
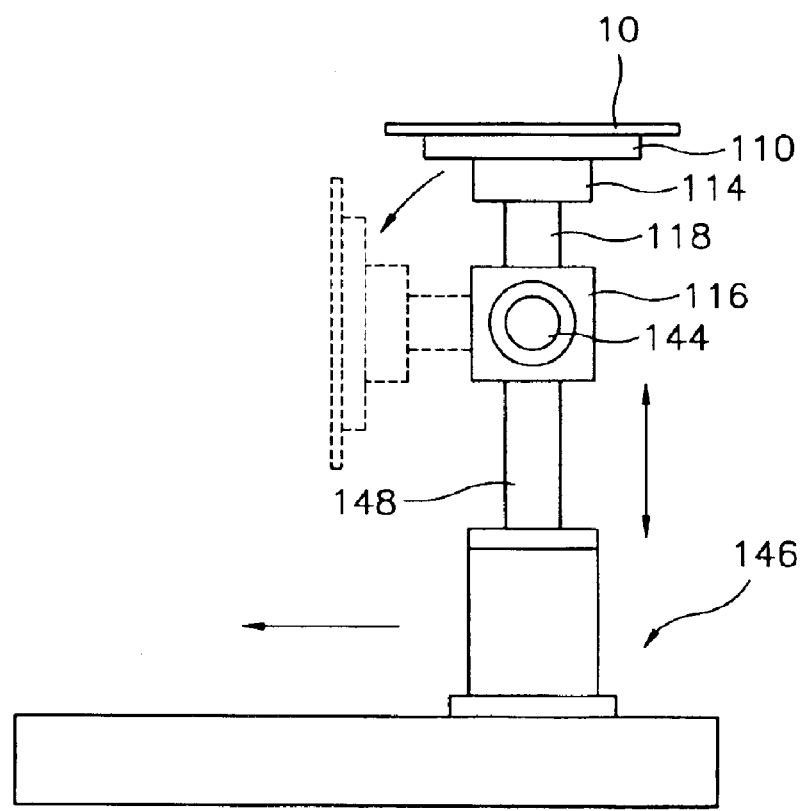
FIG. 4 illustrates a front view of the rotary chuck as shown in FIG. 1.

FIG. 3 illustrates a plan view of a rotary chuck shown in FIG. 1. FIG. 4 illustrates a front view of the rotary chuck shown in FIG. 1

Referring to FIGS. 3 and 4, a vacuum channel 112 is formed radially and circumferentially at an upper surface of the rotary chuck 110. The vacuum force for holding the semiconductor wafer 10 is provided in the vacuum channel 112. A first motor 114 for rotating the rotary chuck 110 is connected to a lower surface of the rotary chuck 110. The first driving unit 144 for tilting the rotary chuck 110 is disposed under the first motor 114. A connecting section 116 and a first driving shaft 118 connect the first motor 114 and the first driving unit 144, and the connecting section 116 is rotatably coupled to the first driving shaft 118.

A second driving unit 146 for moving the rotary chuck 110 horizontally and vertically is disposed under the connecting section 116, and is supported on a bottom panel of the process chamber 102. A second driving shaft 148 connects the second driving unit 146 and the connecting section 116. To collect the second impurities from the edge portion of the tilted semiconductor wafer 10, the second driving unit 146 moves the rotary chuck 110 upwardly, and moves the rotary chuck 110 horizontally toward the second scanning unit 190.

The rotary chuck 110 is disposed over the base panel 104 of the process chamber 102, and is connected to the first driving unit 144 and the second driving unit 146 through the penetrating hole 104a of the base panel 104 shown in FIGS. 1 and 2. The penetrating hole 104a of FIGS. 1 and 2 extends along a horizontal moving direction of the rotary chuck 110.

Figure 5:
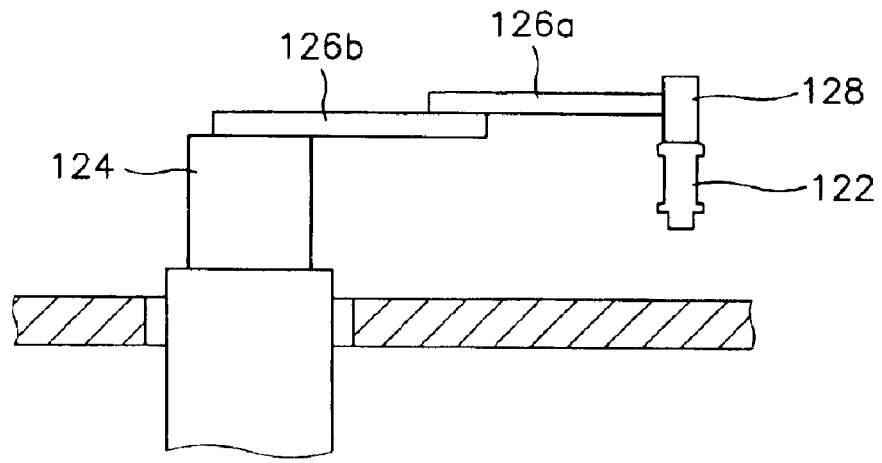
FIG. 5 illustrates a front view of a first scanning unit of FIG. 1.
Figure 6:
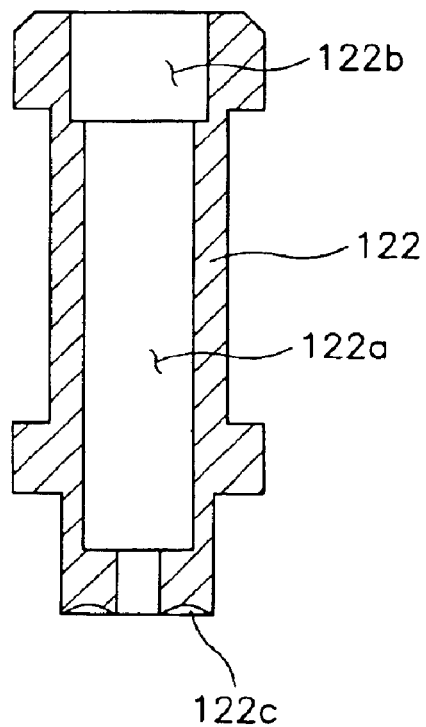
FIG. 6 illustrates a cross-sectional view of a scanning nozzle as shown in FIG. 5.
Figure 7:
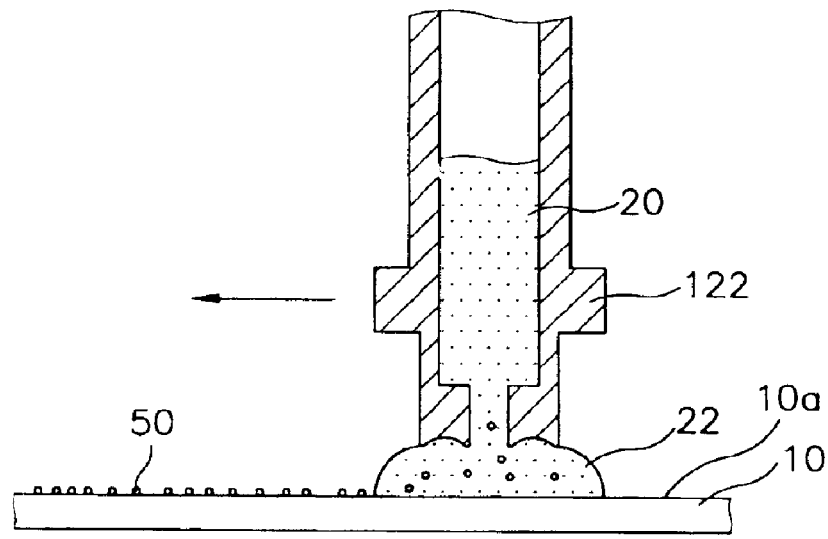
FIG. 7 illustrates a cross-sectional view of a droplet of a first scanning solution and a scanning nozzle.
Figure 8:
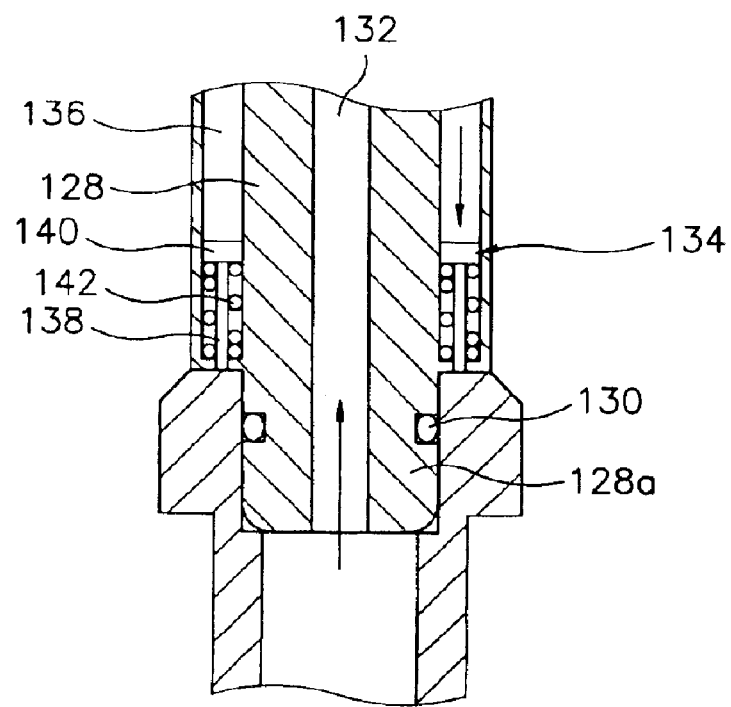
FIG. 8 illustrates a cross-sectional view of the scanning nozzle and a coupling section.

FIG. 5 illustrates a front view of a first scanning unit as shown in FIG. 1. FIG. 6 illustrates a cross-sectional view of a scanning nozzle as shown in FIG. 5. FIG. 7 illustrates a cross-sectional view of a droplet of a first scanning solution and the scanning nozzle. FIG. 8 illustrates a cross-sectional view of the scanning nozzle and a coupling section.

Referring to FIGS. 5 through 8, the first scanning unit 120 preferably includes a scanning nozzle 122 for forming a droplet 22 of the first scanning solution and a scanning robot 124 for moving the scanning nozzle 122 horizontally so that the droplet 22 of the first scanning solution scans an upper surface 10a of the semiconductor wafer 10.

Preferably, a SCARA (Selective Compliance Assembly Robot Arm) type robot is used as the scanning robot 124. However, examples of the scanning robot 124 may include a Cartesian robot, an articulate robot, or the like.

The scanning robot 124 has a first scanning arm 126a and a second scanning arm 126b. The first scanning arm 126a is rotatably coupled to the second scanning arm 126b. The second scanning arm 126b is rotatably coupled to a body of the scanning robot 124. A coupling section 128 for coupling with the scanning nozzle is downwardly extended from an end of the first scanning arm 126a. The scanning robot 124 is disposed on the bottom panel of the process chamber 102, and is upwardly extended through the base panel 104.

The scanning nozzle 122 has a cylindrical shape. Also, the scanning nozzle 122 has a circular hole 122a formed through the scanning nozzle and a coupling groove 122b formed at an inner surface of the circular hole 122a adjacent to an upper surface of the scanning nozzle 122. The circular hole 122a is formed along a central axis of the scanning nozzle 122, and the first scanning solution is received in the circular hole 122a. The coupling groove 122b is downwardly extended from the upper surface of the scanning nozzle 122, and the coupling section 128 of the scanning robot 124 is inserted into the coupling groove 122b to couple the scanning nozzle 122 to the scanning robot 124. Thus, the scanning robot 124 can grasp a scanning nozzle 122. An inner diameter of a lower portion of the circular hole 122a is larger than that of a central portion of the circular hole 122a.

A doughnut-shaped concave portion 122c is formed at a lower surface of the scanning nozzle 122. When the droplet 22 of the first scanning solution coheres to the lower surface of the scanning nozzle 122, the concave portion 122c is in contact with the droplet 22 of the first scanning solution, and increases a contact area between the scanning nozzle 122 and the droplet 22 of the first scanning solution.

The coupling section 128 has a protrusion 128a for coupling with the scanning nozzle 122. The protrusion 128a is inserted into the coupling groove 122b and has an outer diameter corresponding to an inner diameter of the coupling groove 122b. A seal ring 130, such as an O-ring, is interposed between the protrusion 128a and the coupling groove 122b.

A first air channel 132 for providing a first air pressure is formed through the coupling section 128, the first scanning arm 126a and the second scanning arm 126b. The first air channel 132 is in communication with the circular hole 122a of the scanning nozzle 122 and an air pump (not shown).

The first air pressure is applied to suck a first scanning solution 20 into the circular hole 122a and to form the droplet 22 of the first scanning solution 20. The first air pressure is suitably adjusted such that the droplet 22 of the first scanning solution 20 coheres to the lower surface of the scanning nozzle 122.

The first and second scanning arms 126a and 126b of the scanning robot 124 move the scanning nozzle 122 coupled thereto horizontally, so that the droplet 22 of the first scanning solution 20 formed by the first air pressure scans the upper surface 10a of the semiconductor wafer 10, thereby collecting first impurities 50.

The first scanning arm 126a further includes a nozzle-removing section 134 for removing the scanning nozzle 122 from the coupling section 128. The nozzle-removing section 134 preferably includes a second air channel 136, a rod 138, a piston 140 and a spring 142. The second air channel 136 is formed through the coupling section 128, the first scanning arm 126a and the second scanning arm 126b. A second air pressure is applied into the second air channel 136 in order to remove the scanning nozzle 122 from the coupling section 128. The rod 138 and the piston 140 are disposed in the second air channel 136, and the rod 138 is connected to a lower surface of the piston 140. The second air pressure is applied to an upper surface of the piston 140, and then the rod 138 is downwardly protruded from the coupling section 128 to remove the scanning nozzle 122. The spring 142 is disposed around the rod 138 between the piston 140 and an end portion of the second air channel 136 in order to return the protruded rod 138.

Referring to FIGS. 1 and 2, a nozzle tray 150 and a storage container 152 are disposed on the base panel 104 of the process chamber 102. The nozzle tray 150 supports a plurality of scanning nozzles 122, and the storage container 152 receives the first scanning solution. In addition, a plurality of sampling cups 154, a sampling cup tray 156 and a nozzle-receiving container 158 are suitably disposed on the base panel 104. The plurality of sampling cups 154 receives first samples acquired from the upper surface of the semiconductor wafers 10. The first samples include the first scanning solutions and the first impurities. The sampling cup tray 156 supports the sampling cups 154, and the scanning nozzles 122 used in an impurity collection process on the semiconductor wafers are received in the nozzle-receiving container 158. The nozzle tray 150 has a plurality of nozzle-receiving grooves for receiving the scanning nozzles 122, and the sampling cup tray 156 has a plurality of cup-receiving grooves for receiving the sampling cups 154.

Furthermore, a load cassette 160 is disposed on the base panel 104 in order to receive a plurality of semiconductor wafers to be subjected to the impurity collection process. An unload cassette 162 is disposed on the base panel 104 in order to receive the plurality of semiconductor wafers subjected to the impurity collection process. The load cassette 160 and the unload cassette 162 are disposed opposite to each other, and a transfer robot 164 for transferring the semiconductor wafers is disposed between the load cassette 160 and the unload cassette 162. The transfer robot 164 is supported on the bottom panel of the process chamber 102, and extends upwardly through the base panel 104.

A vapor phase decomposition unit 166 is disposed on the base panel 104 in order to remove an oxide layer or a nitride layer formed on the semiconductor wafer 10 using a hydrofluoric acid (HF) vapor before the impurity collection process. The vapor phase decomposition unit 166 preferably includes an airtight container 168 capable of opening and closing in which the hydrofluoric acid vapor is supplied, and a load plate 170 disposed in the airtight container 168 for supporting the semiconductor wafer 10. The airtight container 168 has a hemispherical shape, and is connected to a vapor source (not shown) for supplying the hydrofluoric acid vapor. Preferably, the hydrofluoric acid vapor supplied into the airtight container 168 has a hydrofluoric acid concentration of about 50%.

The load cassette 160, the rotary chuck 110 and the unload cassette 162 are disposed at angular intervals of 90° about the transfer robot 164. The first scanning unit 120 is disposed opposite to transfer robot 164 centering on the rotary chuck 110. The nozzle tray 150, the storage container 152, the sampling cup tray 156 and the nozzle-receiving container 158 are disposed in an order centering on the first scanning unit 120. Preferably, the nozzle tray 150, the storage container 152, the sampling cup tray 156 and the nozzle-receiving container 158 are diametrically disposed in a working area of the scanning robot 124. The first scanning unit 120, the second scanning unit 190, the transfer robot 164 and the vapor phase decomposition unit 166 are disposed at angular intervals of 90° about the rotary chuck 110.

The transfer robot 164 sequentially transfers the semiconductor wafer 10 from the load cassette 160 to the vapor phase decomposition unit 166, from the vapor phase decomposition unit 166 to the rotary chuck 110, and from the rotary chuck 110 to the unload cassette 162. Though not shown in the figures, the impurity collection apparatus 100 further includes a first lifting unit for putting the semiconductor wafer 10 down onto the load plate 170 of the vapor phase decomposition unit 166 and a second lifting unit for putting the semiconductor wafer 10 down onto the rotary chuck 100.

Figure 9:
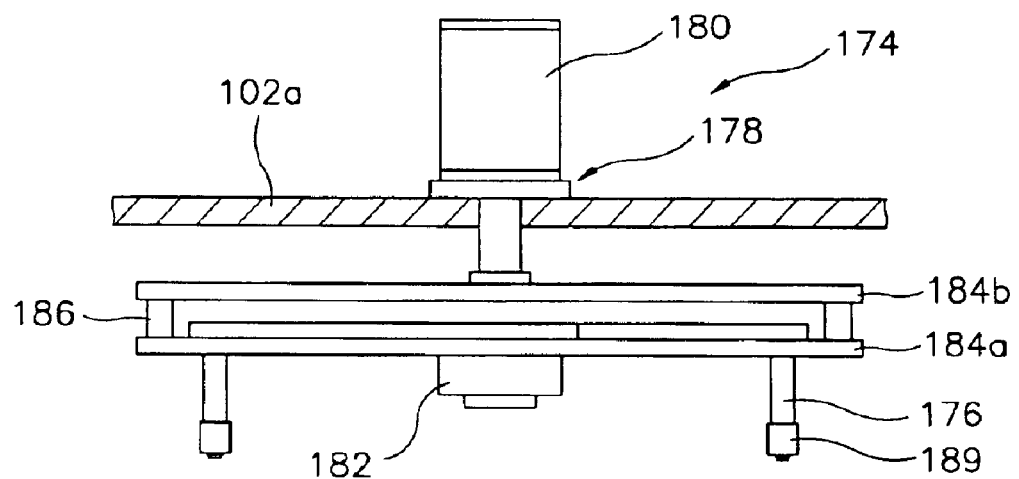
FIG. 9 illustrates a front view of an aligner for aligning a semiconductor wafer.
Figure 10:
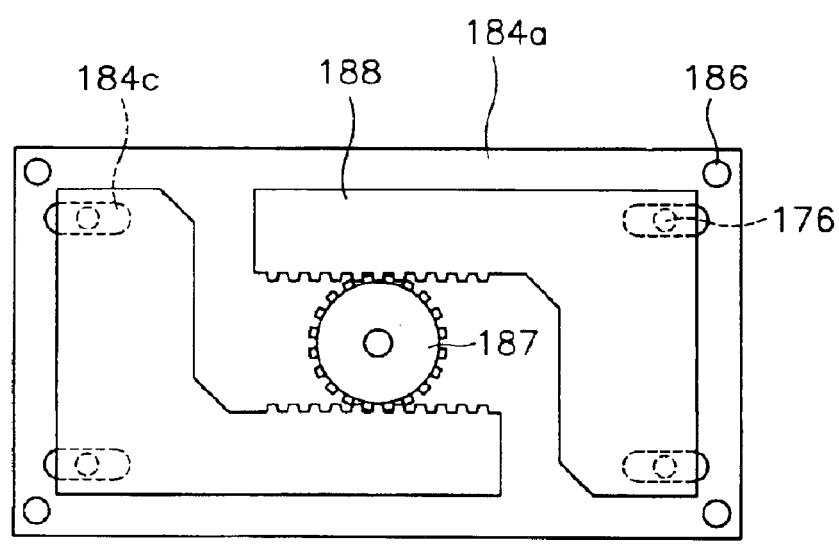
FIG. 10 illustrates a plan view of a rack and pinion as shown in FIG. 9.

FIG. 9 illustrates a front view of an aligner for aligning a semiconductor wafer. FIG. 10 illustrates a plan view of a rack and pinion as shown in FIG. 9.

Referring to FIGS. 9 and 10, and FIGS. 2 and 4, the impurity collection apparatus 100 further includes an aligner 174 for aligning a center of the semiconductor wafer 10 supported on the rotary chuck 110 with a central axis of the rotary chuck 110. The aligner 174 preferably includes a plurality of alignment pins 176 for aligning the center of the semiconductor wafer 10 supported on the rotary chuck 110 with the central axis of the rotary chuck 110, and a third driving unit 178 for moving vertically and horizontally the plurality of alignment pins 176.

The aligner 174 is disposed over the rotary chuck 110. When the semiconductor wafer 10 is placed on the rotary chuck 110, the third driving unit 178 moves the plurality of alignment pins 176 downward so that the alignment pins 176 are placed around the semiconductor wafer 10. The third driving unit 178 then moves the semiconductor wafer 10 simultaneously in a horizontal direction toward the central axis of the rotary chuck 110 such that the center of the semiconductor wafer 10 aligns with the central axis of the rotary chuck 110.

The third driving unit 178 preferably includes a pneumatic cylinder 180 for generating a vertical driving force and a second motor 182 for generating a horizontal driving force.

The pneumatic cylinder 180 is disposed on an upper panel 102a of the process chamber 102 shown in FIG. 1, and the second motor 182 is connected to a lower surface of a lower plate 184a disposed in the process chamber 102. A rod of the pneumatic cylinder 180 extends downwardly through the upper panel 102a of the process chamber 102, and is connected to an upper plate 184b disposed over the lower plate 184a. A plurality of connecting pins 186 connects the lower plate 184a with the upper plate 184b.

A pinion 187 is disposed on the lower plate 184a, and is connected to the second motor 182 through the lower plate 184a. Also, a pair of racks 188 is disposed opposite to each other on the lower plate 184a, and is engaged with the pinion 187. The pinion 187 simultaneously moves the pair of racks 188 in opposite directions from each other to align the semiconductor wafer 10.

Two pairs of alignment pins 176 are connected to the pair of racks 188 through penetrating holes 184c of the lower plate 184a, respectively. The penetrating holes 184c of the lower plate 184a extend in horizontal moving directions of the alignment pins 176. Bearings 189 coupled to ends of the alignment pins 176 are in contact with side portions of the semiconductor wafer 10 during alignment of the semiconductor wafer 10.

Figure 11:
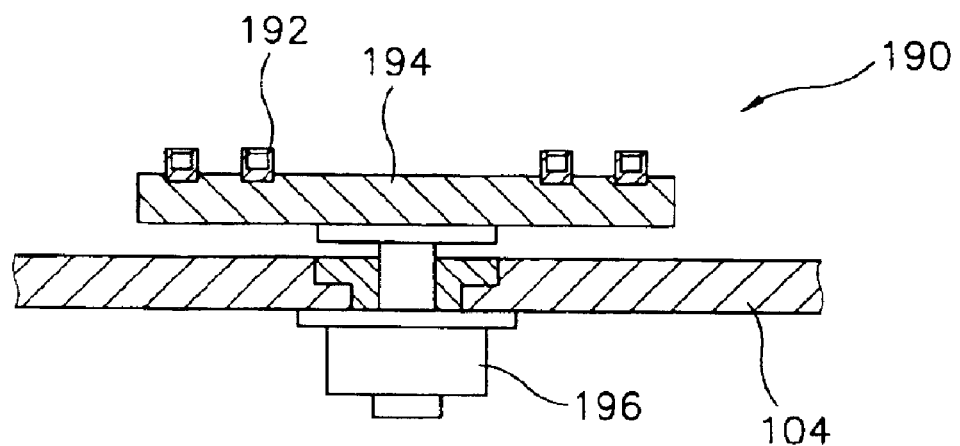
FIG. 11 illustrates a cross-sectional view of a second scanning unit as shown in FIG. 1.
Figure 12:
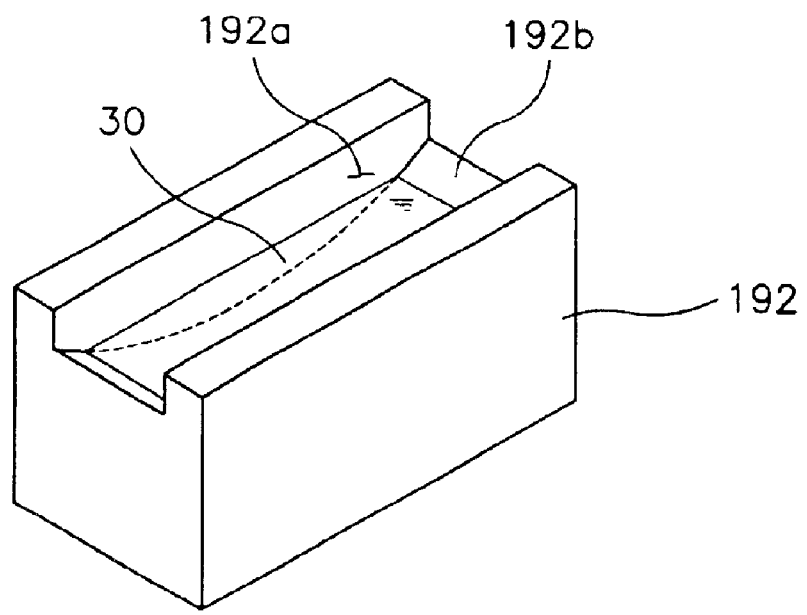
FIG. 12 illustrates a perspective view of a scanning container as shown in FIG. 11.
Figure 13:
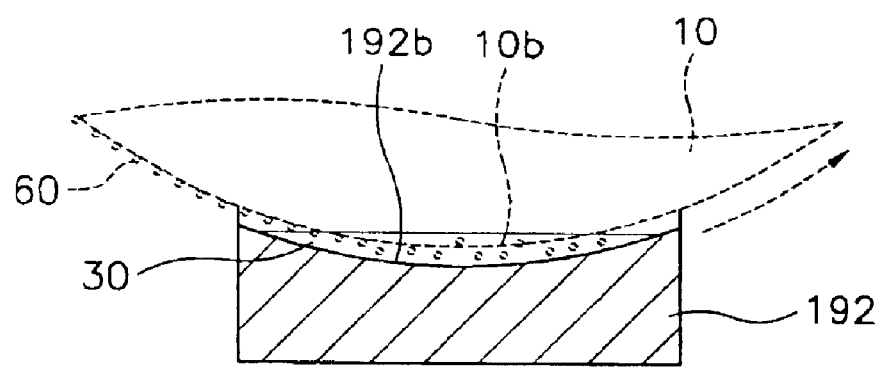
FIG. 13 illustrates a cross-sectional view of the scanning container as shown in FIG. 11.

FIG. 11 illustrates a cross-sectional view of a second scanning unit as shown in FIG. 1. FIG. 12 illustrates a perspective view of a scanning container as shown in FIG. 11. FIG. 13 illustrates a cross-sectional view of the scanning container shown in FIG. 11.

Referring to FIGS. 11 through 13, the second scanning unit 190 preferably includes a plurality of scanning containers 192, a scanning container tray 194 and a fourth driving unit 196. The plurality of scanning containers 192 receives second scanning solution 30 for collecting second impurities 60 from the semiconductor wafers, respectively. The scanning container tray 194 has a disc shape, and the plurality of scanning containers 192 is circumferentially disposed on the scanning container tray 194. Though not shown in the figures, a plurality of container-receiving grooves is circumferentially formed at an upper surface of the scanning container tray 194.

The scanning container tray 194 is disposed over the base panel 104 of the process chamber 102 of FIG. 1. The fourth driving unit 196 coupled to a lower surface of the base panel 104 is connected to the scanning container tray 194 through the base panel 104.

Each of the plurality of the scanning containers 192 has a scanning groove 192a for receiving the second scanning solution 30. The scanning groove 192a is formed at an upper surface of each of the scanning containers 192, and a bottom surface 192b of the scanning groove 192a is a curved surface corresponding to the edge portion 10b of the semiconductor wafer 10.

The first driving unit 144 tilts the semiconductor wafer 10 vertically, and the second driving unit 146 brings an edge portion 10b of the semiconductor wafer 10 into contact with the second scanning solution 30 received in the scanning container 192. The rotary chuck 110 rotates the semiconductor wafer 10 so that the second scanning solution 30 scans the edge portion 10b of the semiconductor wafer 10 thereby collecting the second impurities 60.

FIGS. 14A and 14B, collectively, is a flow chart illustrating a method for collecting impurities on the semiconductor wafer using the apparatus for collecting impurities shown in FIG. 1. The following description of the method for collecting impurities shown in the flow chart of FIGS. 14A and 14B refers to various elements of the apparatus for collecting impurities shown in FIGS. 1–13.

Referring to FIGS. 14A, 14B, and FIGS. 1–13, the transfer robot 164 selects a wafer from the plurality of semiconductor wafers received in the load cassette 160, and transfers the selected semiconductor wafer 10 onto the load plate 170 of the vapor phase decomposition unit 166 (step S10).

The vapor phase decomposition unit 166 removes the oxide layer or the nitride layer formed on the semiconductor wafer 10 supported by the load plate 170 using the hydrofluoric acid vapor (step S20).

The transfer robot 164 transfers the semiconductor wafer 10 from the load plate 170 onto the rotary chuck 110 (step S30).

The aligner 174 aligns the semiconductor wafer 10 supported by the rotary chuck 110 (step S40). The pneumatic cylinder 180 moves the plurality of alignment pins 176 downward, and the second motor 182 moves the plurality of alignment pins simultaneously in a horizontal direction toward the semiconductor wafer 10 such that the center of the semiconductor wafer 10 aligns with the central axis of the rotary chuck 110.

The rotary chuck 110 holds the semiconductor wafer 10 using the vacuum force (step S50).

The scanning robot 124 brings the droplet 22 of the first scanning solution into contact with the upper surface 10a of the semiconductor wafer 10 (step S60). The scanning robot 124 selects one from the plurality of scanning nozzles and moves the selected scanning nozzle 122 to the storage container 152. The scanning nozzle 122 sucks the first scanning solution 20 received in the storage container 152 using the first air pressure. The scanning robot 124 moves the scanning nozzle 122 so that the scanning nozzle 122 is placed over the center of the semiconductor wafer 10. At that time, the first air pressure is suitably adjusted so that the droplet 22 of the first scanning solution coheres to the lower surface of the scanning nozzle 122. The scanning robot 124 moves the scanning nozzle 122 downward so that the droplet 22 of the first scanning solution is in contact with the upper surface 10a of the semiconductor wafer 10.

The droplet 22 of the first scanning solution collects the first impurities 50 from the upper surface 10a of the semiconductor wafer 10 (step S70). The scanning robot 124 moves the scanning nozzle 122 horizontally toward the edge portion of the semiconductor wafer 10. The rotary chuck 110 rotates the semiconductor wafer 10 so that the droplet 22 of the first scanning solution scans the entire upper surface 10a of the semiconductor wafer 10, thereby collecting the first impurities 50. Alternately, the scanning robot 124 may move the droplet 22 of the first scanning solution to collect impurities remaining on a localized portion of the upper surface 10a of the semiconductor wafer 10. The first scanning solution of about 0.2 cc to about 2.5 cc may be used in a process of collecting the first impurities 50. Preferably, the first scanning solution of about 0.5 cc is used in the first impurity collection process.

The sampling cup 154 receives the first scanning solution containing the first impurities 50 (step S80). The scanning nozzle 122 sucks the droplet 22 of the first scanning solution containing the first impurities 50 using the first air pressure. The scanning robot 124 selects one from the plurality of sampling cups, and transfers the scanning nozzle 122 so that the scanning nozzle 122 is placed over the selected sampling cup 154. The suction force applied to scanning nozzle 122 is removed such that the scanning solution containing the first impurities 50 is received in the sampling cup 154. The scanning nozzle 122 used in the first impurity collection process is removed from the scanning robot 124, and is received in the nozzle-receiving container 158.

The first driving unit 144 tilts the semiconductor wafer 10 (step S90) in a vertical direction. The second driving unit 146 moves the rotary chuck 110 upward, and the first driving unit 144 tilts the rotary chuck 110 so that the semiconductor wafer 10 held by the rotary chuck 110 is disposed in the vertical direction.

The second driving unit 146 brings the edge portion 10b of the semiconductor wafer 10 into contact with the second scanning solution 30 (step S100). The second driving unit 146 moves the rotary chuck 110 horizontally so that the semiconductor wafer 10 vertically disposed by the first driving unit 144 is placed above the scanning container tray 194. The fourth driving unit 196 rotates the scanning container tray 194 so that the edge portion 10b of the semiconductor wafer 10 corresponds to one of the plurality of scanning containers 192 supported by the scanning container tray 194. The second driving unit 146 moves the rotary chuck 110 downward such that the edge portion 10b of the semiconductor wafer 10 is in contact with the second scanning solution 30 received in the scanning container 192.

The second scanning solution 30 collects the second impurities 60 from the edge portion 10b of the semiconductor wafer 10 (step S110). The rotary chuck 110 rotates the semiconductor wafer 10 so that the second scanning solution 30 scans the edge portion 10b of the semiconductor wafer 10 thereby collecting the second impurities 60. Preferably, the second scanning solution 30 of about 1 cc to about 2 cc is used in the second impurity collection process.

The first and second driving units 144 and 146 return the semiconductor wafer 10 to an initial position (step S120). The second driving unit 146 moves the rotary chuck 110 upward and moves the rotary chuck 110 horizontally toward the initial position. The first driving unit 144 tilts the rotary chuck 110 horizontally, and the second driving unit 146 moves the rotary chuck 110 downward to the initial position.

The transfer robot 164 transfers the semiconductor wafer 10 subjected to the impurity collection process into the unload cassette 162 (step S130).

The first and second scanning solutions 20 and 30 containing the first and second impurities 50 and 60, respectively, may be analyzed using an analysis apparatus, such as an atomic absorption spectroscope, an inductively coupled plasma (ICP) mass spectroscope, a total X-ray fluorescent analyzer or the like.

Figure 15:
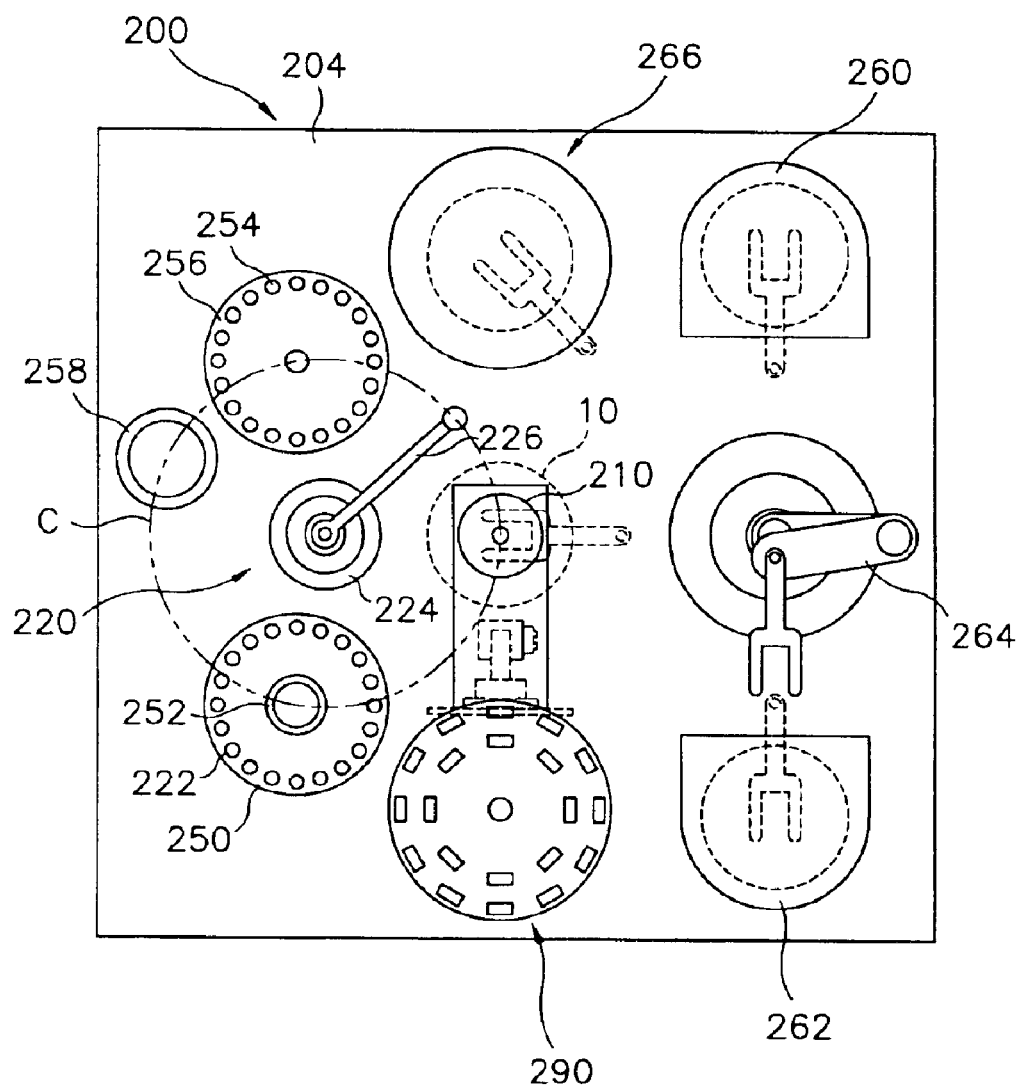
FIG. 15 illustrates a plan view of an apparatus for collecting impurities according to another embodiment of the present invention.
Figure 16:
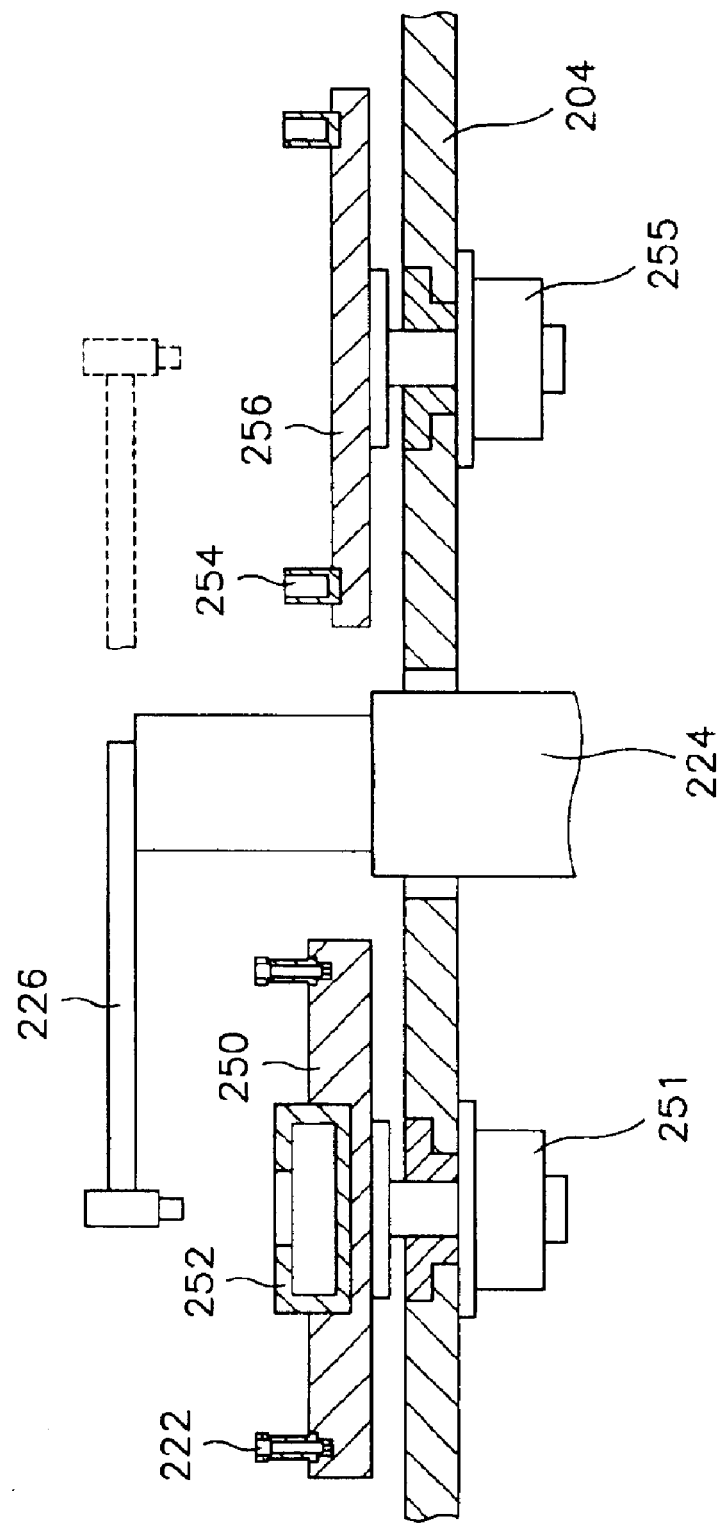
FIG. 16 illustrates a cross-sectional view of a first scanning unit as shown in FIG. 15.

FIG. 15 illustrates a plan view of an apparatus for collecting impurities according to another embodiment of the present invention. FIG. 16 illustrates a cross-sectional view of a first scanning unit as shown in FIG. 15.

Referring to FIGS. 15 and 16, an impurity collection apparatus 200 preferably includes a process chamber (not shown) and a plurality of elements disposed on a base panel 204 of the process chamber.

A load cassette 260 and an unload cassette 262 are disposed opposite to each other on the base panel 204. A transfer robot 264 is disposed between the load cassette 260 and the unload cassette 262 through the base panel 204. In addition, a rotary chuck 210 for supporting a semiconductor wafer 10 and a vapor phase decomposition unit 266 for removing an oxide layer or a nitride layer from the semiconductor wafer 10 are disposed on the base panel 204.

A first scanning unit 220 for collecting first impurities from an upper surface of the semiconductor wafer 10 is disposed opposite to the transfer robot 264 about the rotary chuck 210. A second scanning unit 290 for collecting second impurities from an edge portion of the semiconductor wafer 10 is disposed opposite to the vapor phase decomposition unit 266 about the rotary chuck 210. Preferably, the first scanning unit 220, the second scanning unit 290, the transfer robot 264 and the vapor phase decomposition unit 266 are disposed at angular intervals of 90° about the rotary chuck 210.

The first scanning unit 220 preferably includes a scanning nozzle 222 for forming a droplet of a first scanning solution and a scanning robot 224 for moving the scanning nozzle 222 horizontally so that the droplet of the first scanning solution scans the upper surface of the semiconductor wafer 10. An example of the scanning robot 224 may include a cylindrical robot.

The scanning robot 224 includes a scanning arm 226 capable of rotation. A nozzle-coupling section coupled with the scanning nozzle 222 and a nozzle-removing section for removing the scanning nozzle 222 from the nozzle-coupling section are coupled to an end of the scanning arm 226. The scanning robot 224 is supported on a bottom panel of the process chamber and extends upwardly through the base panel 204.

The scanning nozzle 222 sucks the first scanning solution using a first air pressure, and the first air pressure is suitably adjusted so that the droplet of the first scanning solution coheres to a lower surface of the scanning nozzle 222. The scanning robot 224 moves the scanning nozzle 222 horizontally such that the droplet of the first scanning solution scans the upper surface of the semiconductor wafer 10, thereby collecting the first impurities.

A scanning nozzle tray 250, a sampling cup tray 256 and a nozzle-receiving container 258 are disposed centering on the first scanning unit 220 on the base panel 204. The scanning nozzle tray 250 supports a plurality of the scanning nozzles 222, the sampling cup tray 256 supports a plurality of sampling cups 254, and the nozzle-receiving container 258 receives the scanning nozzles used in the impurity collection process. The scanning nozzle tray 250 and the sampling cup tray 256 are disposed opposite to each other, and the first scanning unit 220 is disposed between the scanning nozzle tray 250 and the sampling cup tray 256.

The scanning nozzle tray 250 has a disc shape, and the plurality of scanning nozzles 222 is supported at regular intervals in a circumferential direction of the scanning nozzle tray 250. A plurality of nozzle-receiving grooves for receiving the plurality of scanning nozzles 222 is circumferentially formed at an upper surface of the scanning nozzle tray 250. The scanning nozzle tray 250 is disposed over the base panel 204, and a fifth driving unit 251 for rotating the scanning nozzle tray 250 is coupled to a lower surface of the base panel 204, and is connected to the scanning nozzle tray 250 through the base panel 204.

A storage container 252 for storing the first scanning solution is disposed on a central portion of the scanning nozzle tray 250.

The sampling cup tray 256 has a disc shape, and the plurality of sampling cups 254 is supported at regular intervals in a circumferential direction of the sampling cup tray 256. A plurality of cup-receiving grooves for receiving the plurality of sampling cups 254 is circumferentially formed at an upper surface of the sampling cup tray 256. The sampling cup tray 256 is disposed over the base panel 204, and a sixth driving unit 255 for rotating the sampling cup tray 256 is coupled to the lower surface of the base panel 204 and is connected to the sampling cup tray 256 through the base panel 204.

Preferably, the scanning nozzle tray 250, the rotary chuck 210, the sampling cup tray 256 and the nozzle-receiving container 258 are disposed along a circle C corresponding to a rotating movement of the scanning nozzle 222 when coupled to the scanning arm 226.

Further detailed descriptions of these elements will be omitted because these elements are similar to those already described in connection with the impurity collection apparatus 100 shown in FIGS. 1 and 2.

Figure 17:
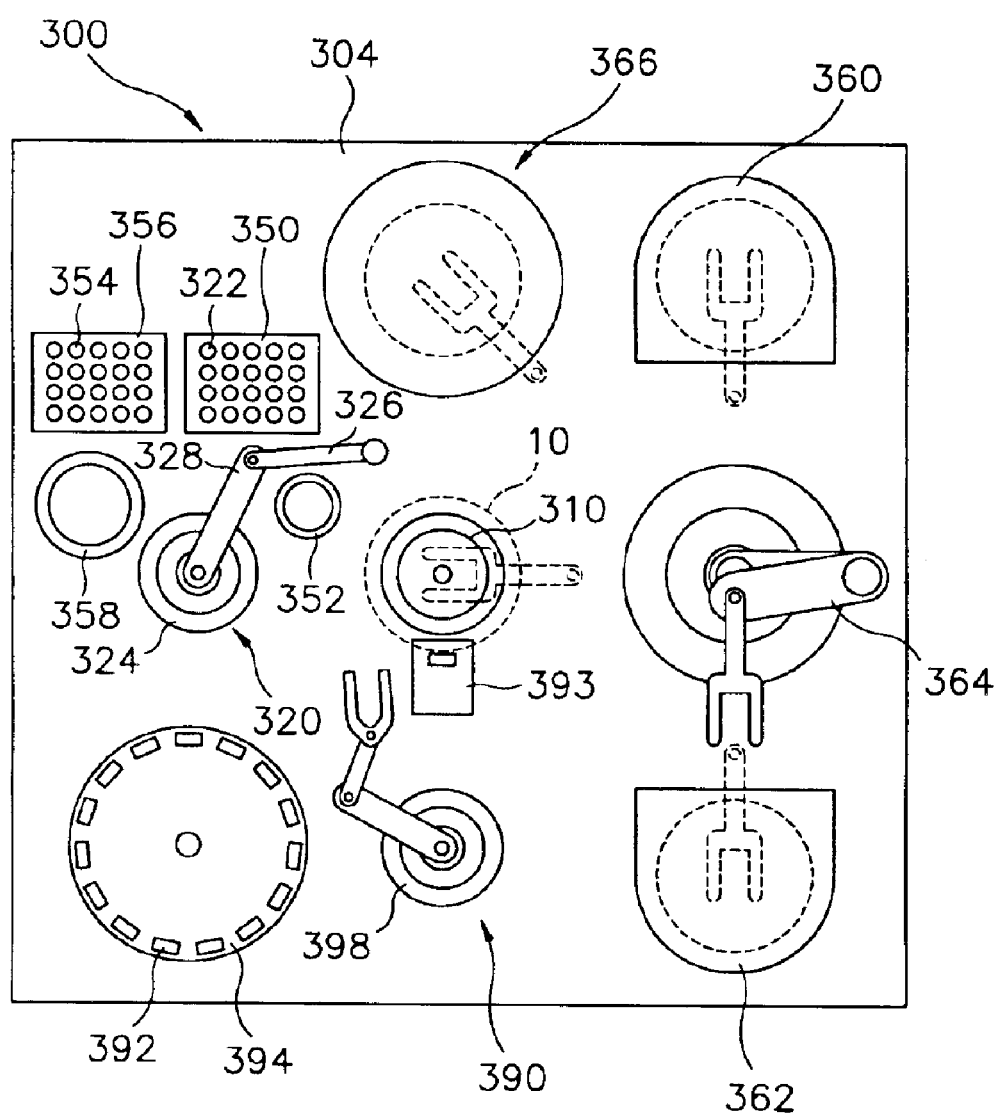
FIG. 17 illustrates a plan view of an apparatus for collecting impurities according to still another embodiment of the present invention.
Figure 18:
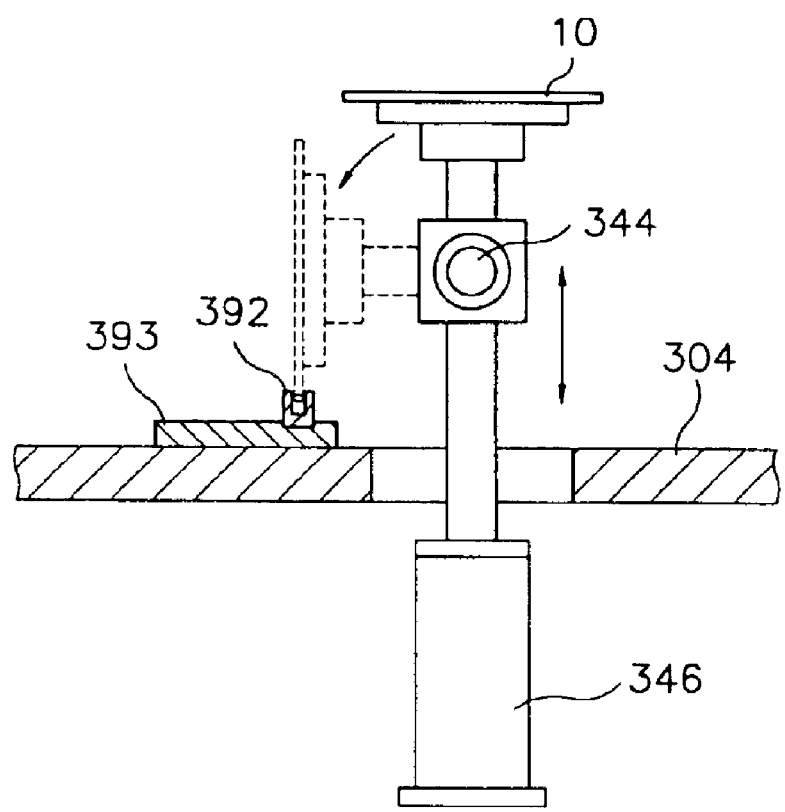
FIG. 18 illustrates a cross-sectional view of a scanning container stage as shown in FIG. 17.
Figure 19:
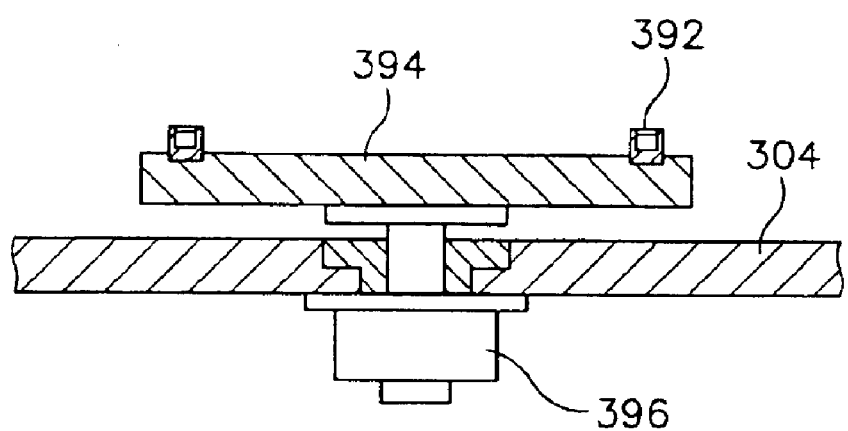
FIG. 19 illustrates a cross-section view of a scanning container tray as shown in FIG. 17.

FIG. 17 illustrates a plan view of an apparatus for collecting impurities according to still another embodiment of the present invention. FIG. 18 illustrates a cross-sectional view of a scanning container stage as shown in FIG. 17. FIG. 19 illustrates a cross-section view of a scanning container tray as shown in FIG. 17.

Referring to FIGS. 17 through 19, an impurity collection apparatus 300 preferably includes a process chamber (not shown) and a plurality of elements disposed on a base panel 304 of the process chamber.

A load cassette 360 and an unload cassette 362 are disposed opposite to each other on the base panel 304. A first transfer robot 364 is disposed between the load cassette 360 and the unload cassette 362 through the base panel 304. In addition, a rotary chuck 310 for supporting a semiconductor wafer 10 and a vapor phase decomposition unit 366 for removing an oxide layer or a nitride layer on the semiconductor wafer 10 are disposed on the base panel 304.

A first scanning unit 320 for collecting first impurities from an upper surface of the semiconductor wafer 10 is disposed opposite to the first transfer robot 364 about the rotary chuck 310. A second scanning unit 390 for collecting second impurities from an edge portion of the semiconductor wafer 10 is disposed opposite to the vapor phase decomposition unit 366 about the rotary chuck 310. Preferably, the first scanning unit 320, the second scanning unit 390, the first transfer robot 364 and the vapor phase decomposition unit 366 are disposed at angular intervals of 90° about the rotary chuck 310.

The first scanning unit 320 preferably includes a scanning nozzle 322 for forming a droplet of a first scanning solution and a scanning robot 324 for moving the scanning nozzle 322 horizontally so that the droplet of the first scanning solution scans the upper surface of the semiconductor wafer 10.

The scanning robot 324 has a first scanning arm 326 and a second scanning arm 328 capable of rotation. A nozzle-coupling section for coupling to the scanning nozzle 322, and a nozzle-removing section for removing the scanning nozzle 322 from the nozzle-coupling section are coupled to an end of the first scanning arm 326. The scanning robot 324 is supported on a bottom panel of the process chamber and extends upwardly through the base panel 304.

The scanning nozzle 322 coupled to the scanning robot 324 via the coupling section of the first scanning arm 326 sucks the first scanning solution using a first air pressure, and the first air pressure is suitably adjusted so that a droplet of the first scanning solution coheres to a lower surface of the scanning nozzle 322. The scanning robot 324 moves the scanning nozzle 322 coupled thereto horizontally such that the droplet of the first scanning solution scans the upper surface of the semiconductor wafer 10, thereby collecting the first impurities.

A scanning nozzle tray 350, a storage container 352, a sampling cup tray 356 and a nozzle-receiving container 358 are disposed adjacent to the first scanning unit 320 and the vapor phase decomposition unit 366 on the base panel 304 as shown in FIG. 17. The scanning nozzle tray 350 supports a plurality of the scanning nozzles 322, the storage container 352 receives the first scanning solution, the sampling cup tray 356 supports a plurality of sampling cups 354, and the nozzle-receiving container 358 receives the scanning nozzles 322 used in the impurity collection process.

The second scanning unit 390 preferably includes a scanning container 392 for receiving a second scanning solution, a stage 393 for supporting the scanning container 392 during wafer scanning, a scanning container tray 394 for supporting a plurality of the scanning containers 392, a second transfer robot 398 for transferring the scanning container 392 between the stage 393 and the scanning container tray 394.

The stage 393 is disposed adjacent to the rotary chuck 310 on the base panel 304 so that the edge portion of the semiconductor wafer 10 tilted vertically by a first driving unit 344 is placed over the scanning container 392 supported on the stage 393. A second driving unit 346 moves the rotary chuck 310 downward so that the edge portion of the semiconductor wafer 10 is in contact with the second scanning solution received in the scanning container 392. The rotary chuck 310 rotates the semiconductor wafer 10 such that the second scanning solution scans the edge portion of the semiconductor wafer 10 thereby collecting the second impurities.

The scanning container tray 394 has a disc shape, and is disposed adjacent to the first scanning unit 320 and the second transfer robot 398. A plurality of the scanning containers 392 is supported at regular intervals in a circumferential direction of the scanning container tray 394. A plurality of container-receiving grooves for receiving the plurality of scanning containers 392 is circumferentially formed at an upper surface of the scanning container tray 394. The scanning container tray 394 is disposed over the base panel 304, and a third driving unit 396 for rotating the scanning container tray 394 is coupled to a lower surface of the base panel 304, and is connected to the scanning container tray 394 through the base panel 304.

Further detailed descriptions of these elements will be omitted because these elements are similar to those already described in connection with the impurity collection apparatus 100 shown in FIGS. 1 and 2.

According to an embodiment of the present invention, the first scanning unit collects the first impurities from the upper surface of the semiconductor wafer, and the second scanning unit collects the second impurities from the edge portion of the semiconductor wafer. The contamination analysis process on the semiconductor wafer is performed using samples containing the first and second impurities, and thus the reliability of the contamination analysis process may be improved.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for collecting impurities on a semiconductor wafer, comprising:
   an airtight process chamber;
   a rotary chuck disposed in the process chamber for horizontally supporting the semiconductor wafer thereon and for rotating the semiconductor wafer;
   a first scanning unit for forming a droplet of a first scanning solution and for scanning an upper surface of the semiconductor wafer rotated by the rotary chuck with the droplet of the first scanning solution to collect first impurities from the upper surface of the semiconductor wafer;

a first driving unit for tilting the rotary chuck to tilt the semiconductor wafer supported on the rotary chuck; and a second scanning unit for receiving a second scanning solution in order to collect second impurities from an edge portion of the semiconductor wafer, the second scanning solution received in the second scanning unit being in contact with the edge portion of the semiconductor wafer tilted by the driving unit and rotated by the rotary chuck so that the second scanning solution scans the edge portion of the semiconductor wafer.

2. The apparatus as claimed in claim 1, further comprising a second driving unit for moving the rotary chuck in horizontal and vertical directions.

3. The apparatus as claimed in claim 1, wherein the first scanning unit comprises:

a scanning nozzle for forming the droplet of the first scanning solution; and a scanning robot coupled to the scanning nozzle for horizontally moving the scanning nozzle so that the droplet of the first scanning solution scans the upper surface of the semiconductor wafer.

4. The apparatus as claimed in claim 3, wherein the scanning robot is a SCARA type robot.

5. The apparatus as claimed in claim 4, further comprising a circular hole for receiving the first scanning solution formed through the scanning nozzle; and a coupling groove for coupling the scanning nozzle to a scanning arm of the scanning robot formed at an inner surface of the circular hole adjacent to an upper surface of the scanning nozzle.

6. The apparatus as claimed in claim 5, further comprising a concave portion formed at a lower surface of the scanning nozzle for making contact with the droplet of the first scanning solution.

7. The apparatus as claimed in claim 5, wherein the scanning arm comprises a coupling section coupled to the coupling groove, an air channel being in communication with the circular hole and for providing an air pressure in order to form the droplet of the first scanning solution that coheres to a lower surface of the nozzle, and a nozzle-removing section for removing the scanning nozzle from the coupling section.

8. The apparatus as claimed in claim 7, wherein the nozzle-removing section comprises:

a second air channel for providing a second air pressure in order to remove the scanning nozzle from the coupling section;

a rod disposed in the second air channel for removing the scanning nozzle;

a piston connected to the rod for transmitting the second air pressure to the rod so that the rod protrudes outwardly from the second air channel and then pushes the scanning nozzle coupled with the coupling section; and a return spring for returning the rod protruded by the second air pressure.

9. The apparatus as claimed in claim 7, further comprising:

a nozzle tray for supporting a plurality of scanning nozzles; and a storage container for storing the first scanning solution.

10. The apparatus as claimed in claim 3, further comprising:

a plurality of sampling cups for receiving the first scanning solution containing the first impurities; and a sampling cup tray for supporting the plurality of sampling cups.

11. The apparatus as claimed in claim 1, wherein the second scanning unit comprises:

a plurality of scanning containers for receiving the second scanning solution;

a scanning container tray for supporting the plurality of scanning containers, the scanning container tray having a disc shape, and the plurality of scanning containers being circumferentially disposed along an edge portion of the scanning container tray; and a second driving unit for rotating the scanning container tray.

12. The apparatus as claimed in claim 11, wherein each of the plurality of scanning containers has a scanning groove, and a bottom surface of the scanning groove is a curved surface corresponding to the edge portion of the semiconductor wafer.

13. The apparatus as claimed in claim 1, wherein the second scanning unit comprises:

a plurality of scanning containers for receiving the second scanning solution;

a scanning container tray for supporting the plurality of scanning containers;

a scanning container stage disposed under the semiconductor wafer tilted by the driving unit for supporting one of the scanning containers; and a transfer robot for transferring the scanning containers between the scanning container tray and the scanning container stage.

14. The apparatus as claimed in claim 1, further comprising:

a load cassette disposed in the process chamber for receiving a plurality of semiconductor wafers to be subjected to an impurity collection process; and an unload cassette disposed in the process chamber for receiving the plurality of semiconductor wafers subjected to the impurity collection process.

15. The apparatus as claimed in claim 14, further comprising a vapor phase decomposition unit for removing an oxide layer or a nitride layer formed on the semiconductor wafer using a hydrofluoric acid vapor.

16. The apparatus as claimed in claim 15, wherein the vapor phase decomposition unit comprises:

an airtight container capable of opening and closing in which the hydrofluoric acid vapor is supplied; and a load plate disposed in the airtight container for supporting the semiconductor wafer.

17. The apparatus as claimed in claim 16, further comprising a transfer robot for transferring the semiconductor wafer among the load cassette, the vapor phase decomposition unit, the rotary chuck and the unload cassette.

18. The apparatus as claimed in claim 1, further comprising an aligner for aligning a center of the semiconductor wafer supported on the rotary chuck with a central axis of the rotary chuck, wherein the aligner includes:

a plurality of alignment pins for simultaneously moving horizontally toward the central axis of the rotary chuck so that the center of the semiconductor wafer is aligned with the central axis of the rotary chuck; and a second driving unit disposed over the rotary chuck for moving the plurality of alignment pins in horizontal and vertical directions.

19. The apparatus as claimed in claim 1, wherein the first and second scanning solutions include $H_2O$, $H_2O_2$ and HF.

20. A method for collecting impurities on a semiconductor wafer comprising:

rotating the semiconductor wafer;

scanning an upper surface of the semiconductor wafer with a droplet of a first scanning solution in order to collect first impurities from the upper surface of the semiconductor wafer;

receiving the first scanning solution containing the first impurities into a sampling cup;

tilting the semiconductor wafer so that an edge portion of the semiconductor wafer is in contact with a second scanning solution received in a scanning container; and rotating the tilted semiconductor wafer in order to collect second impurities from the edge portion of the semiconductor wafer.

* * * * *